United States Patent [19]

Nagai et al.

[11] Patent Number: 4,707,557

[45] Date of Patent: Nov. 17, 1987

[54] 1,1-DICHLORO-1,2,2-TRIMETHYL-2-PHENYLDISILANE AND METHOD FOR PRODUCING THE SAME

[75] Inventors: Yoichiro Nagai, Yamato; Hamao Watanabe; Yoshinori Akutsu, both of Kiryu, all of Japan

[73] Assignee: Yuki Gosei Kogyo Co., Ltd., Tokyo, Japan

[21] Appl. No.: 11,804

[22] Filed: Feb. 6, 1987

[30] Foreign Application Priority Data

Feb. 19, 1986 [JP] Japan .................................. 61-32807

[51] Int. Cl.$^4$ ............................................... C07F 7/08
[52] U.S. Cl. .................................................. 556/430
[58] Field of Search ......................................... 556/430

[56] References Cited

U.S. PATENT DOCUMENTS 4,309,556  1/1982  Allain et al. ........................ 556/430

FOREIGN PATENT DOCUMENTS 0721443  3/1980  U.S.S.R. ............................. 556/430

Primary Examiner—Paul F. Shaver
Attorney, Agent, or Firm—Flynn, Thiel, Boutell & Tanis

[57] ABSTRACT

This invention relates to a novel asymmetric 1,1-dichloro-1,2,2-trimethyl-2-phenyldisilane expressed by the chemical formula (I), $(C_6H_5)(CH_3)_2SiSi(CH_3)Cl_2$.

This invention further relates to a method for producing 1,1-dichloro-1,2,2-trimethyl-2-phenyl disilane by reacting 1,1,2-trichloro-1,2,2-trimethyl disilane expressed by the chemical formula (III), $Cl(CH_3)_2SiSi(CH_3)Cl_2$ with phenyl magnesium halide expressed by the general formula (IV), $C_6H_5MgX$ (X=halogen atom) in the presence of a transition metal (except for cobalt) catalyst.

13 Claims, No Drawings

1,1-DICHLORO-1,2,2-TRIMETHYL-2-PHENYL-DISILANE AND METHOD FOR PRODUCING THE SAME

BACKGROUND OF THE INVENTION (i) Field of the Invention

This invention relates to 1,1-dichloro-1,2,2-trimethyl-2-phenyldisilane which is a novel asymmetric functional disilane, and a method for producing the same.

(ii) Description of the Prior Art

Heretofore, there is no prior arts which show a method for selectively introducing an aryl group into a disilane structure such as 1,1,2-trichloro-1,2,2-trimethyldisilane, and 1,1-dichloro-1,2,2-trimethyl-2-phenyldisilane prepared by selectively substituting one chloro group of the position "2-" of 1,1,2-trichloro-1,2,2-trimethyldisilane with phenyl group is a novel compound which has not been described in any prior arts.

SUMMARY OF THE INVENTION

An object of the present invention is to provide a novel asymmetric functional disilane, i.e. 1,1-dichloro-1,2,2-trimethyl-2-phenyldisilane expressed by the chemical formula (I), $(C_6H_5)(CH_3)_2SiSi(CH_3)Cl_2$ (hereinafter referred to as "Disilane I").

Another object of the present invention is to provide a method for producing 1,1-dichloro-1,2,2-trimethyl-2-phenyldisilane (Disilane I) by reacting 1,1,2-trichloro-1,2,2-trimethyldisilane expressed by the chemical formula (III), $Cl(CH_3)_2SiSi(CH_3)Cl_2$ (hereinafter referred to as "Disilane III") with phenyl magnesium halide expressed by the general formula (IV), $C_6H_5MgX$ (X=halogen atom) (hereinafter referred to as "reagent") in the presence of a transition metal (except for cobalt) catalyst.

DETAILED DESCRIPTION OF THE INVENTION

Disilane I of the present invention is a compound useful as an intermediate for polysilane having various functions as an electroconductor, photoresist, optical information recording material or the like.

There is a proposal for preparing Disilane I by the reaction of Disilane III with a Grignard reagent. However, if this reaction is carried out in the absence of a catalyst, in addition to the desired 1,1-dichlorodisilane type Disilane I, 1,2-dichlorodisilane type 1,2-dichloro-1,2,2-trimethyl-1-phenyldisilane expressed by the chemical formula (II), $Cl(CH_3)_2SiSi(CH_3)(C_6H_5)Cl$ (hereinafter referred to as "Disilane II") is also produced. Disilane I and Disilane II are produced in a ratio of about 1 : 1. Thus, this method has a disadvantage that Disilane I or Disilane II can not be produced selectively.

We have studied a method for selectively producing Disilane I alone from Disilane III, and have found that Disilane I alone can be selectively produced at a favourable yield by reacting Disilane III with a Grignard reagent in the presence of a transition metal (except for cobalt) catalyst. The present invention is based on this finding.

The production step of Disilane I in accordance with the present invention can be illustrated by the following chemical reaction formula.

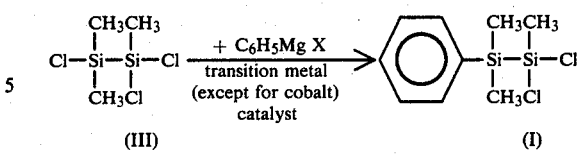

Examples of a transition metal (except for cobalt) catalyst used in the present invention include copper and nickel halides such as cuprous chloride (CuCl), cuprous iodide (CuI), nickel chloride ($NiCl_2$) and the like, but should not be limited thereto.

Disilane III used as the starting material in the present invention can be obtained by a disilane fraction by-produced when producing dichlorodimethyl silane from methyl chloride and metallic silicon.

Examples of a Grignard reagent used in the present invention include phenyl magnesium halide such as phenyl magnesium iodide, phenyl magnesium bromide, phenyl magnesium chloride and the like.

According to this invention, 1 equivalent of Disilane III is reacted with 0.9 to 1.1 equivalent of a Grignard reagent in the presence of 0.01 to 0.1 equivalent of a transition metal (except for cobalt) catalyst in an aprotic solvent such as n-hexane, tetrahydrofuran, diethyl ether, toluene, benzene or the like. The preferable reaction temperature is 0 to 50° C., and the reaction is generally completed in 1 to 12 hours. However, the reaction is not limited to these reaction conditions. After the reaction, the product is purified by normal purification method. Thus, Disilane I of a high purity can be obtained at a high yield of 90% or more.

The present invention selectively provides 1,1-dichlorodisilane type Disilane I alone at a favourable yield by the reaction of Disilane III with a Grignard reagent in the presence of a transition metal (except for cobalt) catalyst.

Disilane III used as the starting material in the present invention can be obtained by a disilane fraction by-produced at a yield of 10 to 20% when producing dichlorodimethylsilane from methyl chloride and metallic silicon. The disilane fraction thus by-produced is at present disposed or stored without being utilized. Thus, the present invention effectively utilizes unused resourses.

The present invention is further illustrated by the following Examples and Comparative Example.

COMPARATIVE EXAMPLE 1,1,2-trichloro-1,2,2-trimethyldisilane 103.8 g (0.5 mole) and diethyl ether 200 g were placed in a one liter four-necked flask equipped with a condenser, dropping funnel, thermometer and stirrer, and a diethyl ether solution of phenyl magnesium bromide 90.5 g (0.5 mole) was dropwise added thereto for 3 hours while stirring at the reaction temperature of 25° to 30° C. After the dropwise addition, the stirring was continued for 2 hours at 25° to 30° C. to complete the reaction. In order to identify the reaction product, a small amount of the product obtained by separating the by-produced magnesium salt by filtration were reduced with lithium aluminum hydride and the reduced product was subjected to $^1H$-NMR spectrum ($C_6D_6$) analysis. As this result, hydrogens marked (a) and (b) as illustrated by the following chemical formulas could be indentified, and the intensity ratio of them was 1:1.

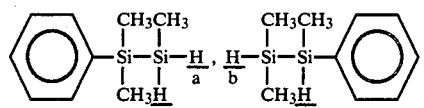

a: 3.2~3.5 ppm (q)
b: 3.6~4.4 ppm (m)

Thus, the reaction product this Comparative Example was proved to be a mixture of 1,1-dichloro-1,2,2-trimethyl-2-phenyldisilane and 1,2-dichloro-1,2,2-trimethyl-1-phenyldisilane in a ratio of 1:1.

EXAMPLE 1

1,1,2-trichloro-1,2,2-trimethyldisilane 103.8 g (0.5 mole), cuprous iodide 9.5 g (0.05 mole) and diethyl ether 20 g were placed in the same type of reaction apparatus as used in the above Comparative Example, and a diethyl ether solution of phenyl magnesium bromide 90.5 g (0.5 mole) was dropwise added thereto for 3 hours while stirring at the reactin temperature of 25° to 30° C. After the dropwise addition, the stirring was continued for 2 hours at 25° to 30° C. to complete the reaction. In order to identify the reaction product, the product obtained by separating the by-produced magnesium salt by filtration was subjected to $^1$H-NMR spectrum (C$_6$D$_6$) analysis in the same manner as in the above Comparative Example. As this result, it was proved that the production ratio of 1,1-dichloro-1,2,2-trimethyl-2-phenyldisilane to 1,2-dichloro-1,2,2-trimethyl-1-phenyldisilane was 99 to 1. Thus, the desired Disilane I could be produced at quite a favourable selectivity. The reaction product was then purified by a normal purification method to obtain 1,1-dichloro-1,2,2-trimethyl-2-phenyldisilane 112.2 g at the yield of 90%.

The various properties of the reaction product thus obtained were as follows:
Boiling Point: 128–130° C./20 mmHg.
Mass Spectrum: 249 (M+1).
Proton NMR Spectrum (CCl$_4$):

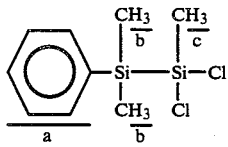

a: 7.1~7.6 ppm (m, 5H)
b: 0.5 ppm (s, 6H)
c: 0.7 ppm (s, 3H)

Infrared Absorption Spectrum (NaCl): (cm$^{-1}$) 3050, 2960, 1585, 1480, 1425, 1400, 1250, 1105.

EXAMPLES 2 TO 3

The same procedure as in Example 1 was repeated, except that the type and amount of the transition metal halide catalyst were changed as described in the following Table 1.

The reaction product thus obtained was subjected to $^1$H-NMR spectrum (C$_6$D$_6$) analysis in the same manner as in the above Comparative Example. The results are shown in the following Table 1.

TABLE 1

| Example | Transition Metal Halide | | Production Ratio of Disilane I/II |
|---|---|---|---|
| | Type | Amount (mole) | |
| 2 | CuCl | 0.05 | 80/20 |
| 3 | CuI | 0.025 | 80/20 |

Note:
Disilane I = 1,1-dichloro-1,2,2-trimethyl-2-phenyl disilane
Disilane II = 1,2-dichloro-1,2,2-trimethyl-1-phenyl disilane

What we claim is:
1. 1,1-dichloro-1,2,2-trimethyl-2-phenyldisilane expressed by the chemical formula (I),

(C$_6$H$_5$)(CH$_3$)$_2$SiSi(CH$_3$)Cl$_2$.

2. A method for producing 1,1-dichloro-1,2,2-trimethyl-2-phenyldisilane by reacting 1,1,2-trichloro-1,2,2-trimethyldisilane expressed by the chemical formula (III), Cl(CH$_3$)$_2$SiSi(CH$_3$)Cl$_2$ with phenyl magnesium halide expressed by the general formula (IV), C$_6$H$_5$MgX (X=halogen atom) in the presence of a transition metal (except for cobalt) catalyst.

3. A method as claimed in claim 2, wherein said transition metal catalyst is copper or nickel halide.

4. A method as claimed in claim 3, wherein said transition metal catalyst is selected from the group consisting of cuprous chloride (CuCl), cuprous iodide (CuI) and nickel chloride (NiCl$_2$).

5. A method as claimed in claim 2, wherein said phenyl magnesium halide is selected from the group consisting of phenyl magnesium iodide, phenyl magnesium bromide and phenyl magnesium chloride.

6. A method as claimed in claim 2, wherein said reaction is carried out in an aprotic solvent.

7. A method as claimed in claim 6, wherein said aprotic solvent is selected from the group consisting of n-hexane, tetrahydrofuran, diethyl ether, toluene and benzene.

8. A method as claimed in claim 2, wherein one equivalent of said 1,1,2-trichloro-1,2,2-trimethyl disilane is reacted with 0.9 to 1.1 equivalent of phenyl magnesium halide in the presence of 0.01 to 0.1 equivalent of a transition metal (except for cobalt) catalyst at a temperature of 0° to 50° C. for 1 to 12 hours.

9. A method as claimed in claim 8, wherein said transition metal catalyst is copper or nickel halide.

10. A method as claimed in claim 9, wherein said transition metal catalyst is selected from the group consisting of cuprous chloride (CuCl), cuprous iodide (CuI) and nickel chloride (NiCl$_2$).

11. A method as claimed in claim 8, wherein said phenyl magnesium hlide is selected from the group consisting of phenyl magnesium iodide, phenyl magnesium bromide and phenyl magnesium chloride.

12. A method as claimed in claim 8, wherein said reaction is carried out in an aprotic solvent.

13. A method as claimed in claim 12, wherein said aprotic solvent is selected from the group consisting of n-hexane, tetrahydrofuran, diethyl ether, toluene and benzene.

* * * * *